United States Patent
Lindstrom

(10) Patent No.: US 10,421,957 B2
(45) Date of Patent: Sep. 24, 2019

(54) DNA ASSEMBLY USING AN RNA-PROGRAMMABLE NICKASE

(71) Applicant: Agilent Technologies, Inc., Loveland, CO (US)

(72) Inventor: Derek Lee Lindstrom, Cupertino, CA (US)

(*) Notice: Subject to any disclaimer, the term of this patent is extended or adjusted under 35 U.S.C. 154(b) by 530 days.

(21) Appl. No.: 14/320,431

(22) Filed: Jun. 30, 2014

(65) Prior Publication Data

US 2015/0031089 A1 Jan. 29, 2015

Related U.S. Application Data

(60) Provisional application No. 61/859,613, filed on Jul. 29, 2013.

(51) Int. Cl.
C12Q 1/68 (2018.01)
C12N 15/10 (2006.01)

(52) U.S. Cl.
CPC .................. *C12N 15/1031* (2013.01)

(58) Field of Classification Search
None
See application file for complete search history.

(56) References Cited

U.S. PATENT DOCUMENTS

| | | |
|---|---|---|
| 2014/0038241 A1 | 2/2014 | Zhou et al. |
| 2014/0127752 A1 | 5/2014 | Zhou et al. |

FOREIGN PATENT DOCUMENTS

| | | |
|---|---|---|
| WO | WO2013141680 | 9/2013 |
| WO | WO2013142578 | 9/2013 |
| WO | WO2013176772 | 11/2013 |
| WO | WO2013188638 | 12/2013 |
| WO | WO2014018423 | 1/2014 |

OTHER PUBLICATIONS

Gasiunas, et al., "Cas9—crRNA ribonucleoprotein complex mediates specific DNA cleavage for adaptive immunity in bacteria", PNAS, E2579-E2586, 2012.
Gnirke, et al., "Solution hybrid selection with ultra-long oligonucleotides for massively parallel targeted sequencing", Nature Biotechnology, 182-189, vol. 27, No. 2, 2009.
Jinek, et al., "RNA-programmed genome editing in human cells", eLife, 1-9, 2013.
Jinek, et al.,"A Programmable Dual-RNA—Guided DNA Endonuclease in Adaptive Bacterial Immunity", Science, 37 pages, 2012.
Lecong, et al., "Multiplex Genome Engineering Using CRISPR/Cas Systems", Science 339, 819-823, 2013.
Qi, et al, "Repurposing CRISPR as an RNA-Guided Platform for Sequence-Specific Control of Gene Expression", Cell, 152, 1173-1183, 2013.
Smolina, et al., "End invasion of peptide nucleic acids (PNAs) with mixed-base composition into linear DNA duplexes", Nucleic Acids Research, 2005, vol. 33, No. 17, 1-9.
Wu, et al., "Genome-wide binding of the CRISCRISCRISCRISPR endonuclease Cas9 in mammalian cells", Nature Biotechnology, 1-9, 2014.

*Primary Examiner* — Bradley L. Sisson

(57) ABSTRACT

This disclosure provides, among other things, a method of combining nucleic acid fragments, comprising: (a) providing two double-stranded DNA molecules with a common sequence, wherein the common sequence is at the end of each molecule; (b) nicking one strand in the common sequence of both molecules at a respective nicked site; (c) moderately denaturing both molecules to remove a single-stranded fragment from the nicked site to one end of each molecule, wherein the single-stranded fragment includes the common sequence in part or in whole, resulting in an overhanging sequence in each molecule, and the overhanging sequences in both molecules are complementary to each other; (d) allowing the overhanging sequences of both molecules to anneal to each other, and ligating the molecules. Alternative ways for performing the method are also provided.

19 Claims, 9 Drawing Sheets

Specification includes a Sequence Listing.

FIG. 8: double stranded DNA sequences of two fragments to be joined

DNA fragment one:
5'-ATATCATCTCCGATGAAGCCTCCG/TTATCCCAGGTTCCTTGG-3' (SEQ ID NO: 1)
3'-TATAGTAGAGGCTACTTCGGAGGC AATAGGGTCCAAGGAACC-5' (SEQ ID NO: 2)

DNA fragment two:
5'-TTATCCCAGGTTCCTTGG GTTTGGTGCCATCTGCGT-3' (SEQ ID NO: 3)
3'-AATAGGGTCCAAGGAACC/CAAACCACGGTAGACGCA-5' (SEQ ID NO: 4)

FIG. 9: Nicked DNA fragments after melting

DNA fragment one:
5'ATATCATCTCCGATGAAGCCTCCG -3' (SEQ ID NO: 5)
3'-TATAGTAGAGGCTACTTCGGAGGCAATAGGGTCCAAGGAACC-5' (SEQ ID NO: 6)

DNA fragment two:
5'-TTATCCCAGGTTCCTTGGGTTTGGTGCCATCTGCGT-3' (SEQ ID NO: 7)
3'- CAAACCACGGTAGACGCA-5' (SEQ ID NO: 8)

FIG. 10: Nicked DNA fragments after annealing

DNA fragment one:
5'ATATCATCTCCGATGAAGCCTCCG/TTATCCCAGGTTCCTTGG GTTTGGTGCCATCTGCGT
-3' (SEQ ID NO: 9)
3'TATAGTAGAGGCTACTTCGGAGGC AATAGGGTCCAAGGAACC/CAAACCACGGTAGACGCA
-5' (SEQ ID NO: 10)

FIG. 11: Double stranded DNA sequences of two fragments to be joined

DNA fragment one:
5'TTTCTGATGTTCGTTCCAATG/TCAAGTTCGATTTCA3'  (SEQ ID NO: 11)
3'AAAGACTACAAGCAAGGTTAC AGTTCAAGCTAAAGT5'  (SEQ ID NO: 12)

DNA fragment two:
    5'TGAAAATCATTTAATTGGCCATGC/TGCGACCGTCAGGG3'  (SEQ ID NO: 13)
    3'ACTTTTAGTAAATTAACCGGTACG ACGCTGGCAGTCCC5'  (SEQ ID NO: 14)

FIG. 12: Nicked DNA fragments after melting

DNA fragment one:
5'TTTCTGATGTTCGTTCCAATG/ 3'  (SEQ ID NO: 15)
3'AAAGACTACAAGCAAGGTTAC AGTTCAAGCTAAAGT5'  (SEQ ID NO: 16)

DNA fragment two:

5'/TGCGACCGTCAGGG3'  (SEQ ID NO: 17)
3'ACTTTTAGTAAATTAACCGGTACG ACGCTGGCAGTCCC5'  (SEQ ID NO: 18)

FIG. 13: Nicked DNA fragments and ssDNA bridge (itaics)after annealing

5'TTTCTGATGTTCGTTCCAATG/TCAAGTTCGATTTCA  *TGAAAATCATTTAATTGGCCATG C*/TGCGACCGTCAGGG3'  (SEQ ID NO: 19)
3'AAAGACTACAAGCAAGGTTAC  AGTTCAAGCTAAAGT/ACTTTTAGTAAATTAACCGGTAC G  ACGCTGGCAGTCCC5'  (SEQ ID NO: 20)

10,421,957 B2

```
                          SEQUENCE LISTING

<160> NUMBER OF SEQ ID NOS: 20

<210> SEQ ID NO 1
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 1
atatcatctc cgatgaagcc tccgttatcc caggttcctt gg                    42

<210> SEQ ID NO 2
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 2
ccaaggaacc tgggataacg gaggcttcat cggagatgat at                    42

<210> SEQ ID NO 3
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 3
ttatcccagg ttccttgggt tggtgccat ctgcgt                            36

<210> SEQ ID NO 4
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 4
acgcagatgg caccaaaccc aaggaacctg ggataa                           36

<210> SEQ ID NO 5
```

```
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 5
atatcatctc cgatgaagcc tccg                                          24

<210> SEQ ID NO 6
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 6
ccaaggaacc tgggataacg gaggcttcat cggagatgat at                      42

<210> SEQ ID NO 7
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 7
ttatcccagg ttccttgggt ttggtgccat ctgcgt                             36

<210> SEQ ID NO 8
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 8
acgcagatgg caccaaac                                                 18

<210> SEQ ID NO 9
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 9
atatcatctc cgatgaagcc tccgttatcc caggttcctt gggtttggtg ccatctgcgt   60

<210> SEQ ID NO 10
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 10
acgcagatgg caccaaaccc aaggaacctg ggataacgga ggcttcatcg gagatgatat   60

<210> SEQ ID NO 11
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 11
```
tttctgatgt tcgttccaat gtcaagttcg atttca            36

<210> SEQ ID NO 12
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 12
tgaaatcgaa cttgacattg gaacgaacat cagaaa            36

<210> SEQ ID NO 13
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 13
tgaaaatcat ttaattggcc atgctgcgac cgtcaggg          38

<210> SEQ ID NO 14
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 14
ccctgacggt cgcagcatgg ccaattaaat gattttca          38

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 15
tttctgatgt tcgttccaat g                            21

<210> SEQ ID NO 16
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 16
tgaaatcgaa cttgacattg gaacgaacat cagaaa            36

<210> SEQ ID NO 17
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 17
tgcgaccgtc aggg                                    14

<210> SEQ ID NO 18
<211> LENGTH: 38
<212> TYPE: DNA

```
<213> ORGANISM: Artificial Sequence
<220> FEATURE:
<223> OTHER INFORMATION: Synthetic oligonucleotide

<400> SEQUENCE: 18
ccctgacggt cgcagcatgg ccaattaaat gattttca                               38

<210> SEQ ID NO 19
<211> LENGTH: 74
<212> TYPE: DNA
<213> ORGANISM: Artificial Sequence
<220> FEATURE:
<223> OTHER INFORMATION: Synthetic oligonucleotide

<400> SEQUENCE: 19
tttctgatgt tcgttccaat gtcaagttcg atttcatgaa aatcatttaa ttggccatgc       60
tgcgaccgtc aggg                                                        74

<210> SEQ ID NO 20
<211> LENGTH: 74
<212> TYPE: DNA
<213> ORGANISM: Artificial Sequence
<220> FEATURE:
<223> OTHER INFORMATION: Synthetic oligonucleotide

<400> SEQUENCE: 20
aaagactaca agcaaggtta cagttcaagc taaagtactt ttagtaaatt aaccggtacg       60
acgctggcag tccc                                                        74
```

DNA ASSEMBLY USING AN RNA-PROGRAMMABLE NICKASE

CROSS-REFERENCING

This patent application claims the benefit of U.S. provisional application Ser. No. 61/859,613, filed on Jul. 29, 2013, which application is incorporated by reference herein.

BACKGROUND

Many methods have been developed to ligate double stranded DNA fragments into larger molecules. Assembly methods that allow the user to dictate the order and orientation of the assembled fragments invariably rely on the specific hybridization of short single-stranded overhangs at the fragment ends. In standard cloning methods, these overhangs are generated by restriction enzymes and are typically only 4 nucleotides long. While 4 nucleotides can provide enough specificity in a simple reaction (e.g., 2-6 fragments), they are not useful for more complicated assemblies. In other methods, the double stranded DNA at fragment ends is converted into single stranded overhangs by an exonuclease. Here the single stranded regions can be hundreds of nucleotides long depending on the processivity of the exonuclease. These long regions of single-stranded DNA can provide very good specificity in an assembly, but the processed ends usually have to be repaired using DNA polymerases that can introduce synthesis errors in the product molecules. Additionally, shorter DNA fragments (e.g., less than ~500 bp) can be entirely degraded by the exonuclease activity before assembly is complete. A third approach is to convert the entire double stranded fragments into single stranded molecules by melting. Complementary regions of homology ~15-500 nucleotides long at the ends of these fragments can then act as primer sites for DNA polymerases to convert the annealed molecules into a double stranded product. Again, this approach is prone to synthesis errors as well as assembly errors due to inadvertent hybridization between regions of homology elsewhere in the molecules.

SUMMARY

This disclosure provides, among other things, a method of combining nucleic acid fragments, comprising: (a) providing two double-stranded DNA molecules with a common sequence, wherein the common sequence is at the end of each molecule; (b) nicking one strand in the common sequence of both molecules at a respective nicked site; (c) moderately denaturing both molecules to remove a single-stranded fragment from the nicked site to one end of each molecule, wherein the single-stranded fragment includes the common sequence in part or in whole, resulting in an overhanging sequence in each molecule, and the overhanging sequences in both molecules are complementary to each other; (d) allowing the overhanging sequences of both molecules to anneal to each other, and ligating the molecules.

Also provided is a method comprising: (a) obtaining a first double-stranded DNA molecule of formula A and a second double-stranded DNA molecule of formula B; (b) nicking: (i) the first fragment of double-stranded DNA at a site that is 4-30 bases from the 3' end of one of the strands of the first fragment, using Cas9 nickase and a first guide RNA; (ii) the second fragment of double-stranded DNA at a site that is 4-30 bases from the 5' end of one of the strands of the second fragment, using Cas9 nickase and a second guide RNA; (c) denaturing the nicked products of (b) in moderately denaturing conditions, thereby producing double-stranded products that comprise overhangs in range of 4-30 bases in length; (d) ligating the double-stranded products of (c) by annealing the overhangs to a splint oligonucleotide and ligating the ends of the products together using a ligase, thereby joining the double-stranded products to the splint oligonucleotide and producing product molecules comprising molecules of the formula A-B.

BRIEF DESCRIPTION OF THE FIGURES

The skilled artisan will understand that the drawings, described below, are for illustration purposes only. The drawings are not intended to limit the scope of the present teachings in any way.

FIGS. 8, 9, and 10 illustrate an example of one embodiment of the method. From top to bottom: SEQ ID NOs: 1-10.

FIGS. 11, 12, and 13 illustrate an example of another embodiment of the method. From top to bottom: SEQ ID NOs: 11-20.

DEFINITIONS

Figure 1:
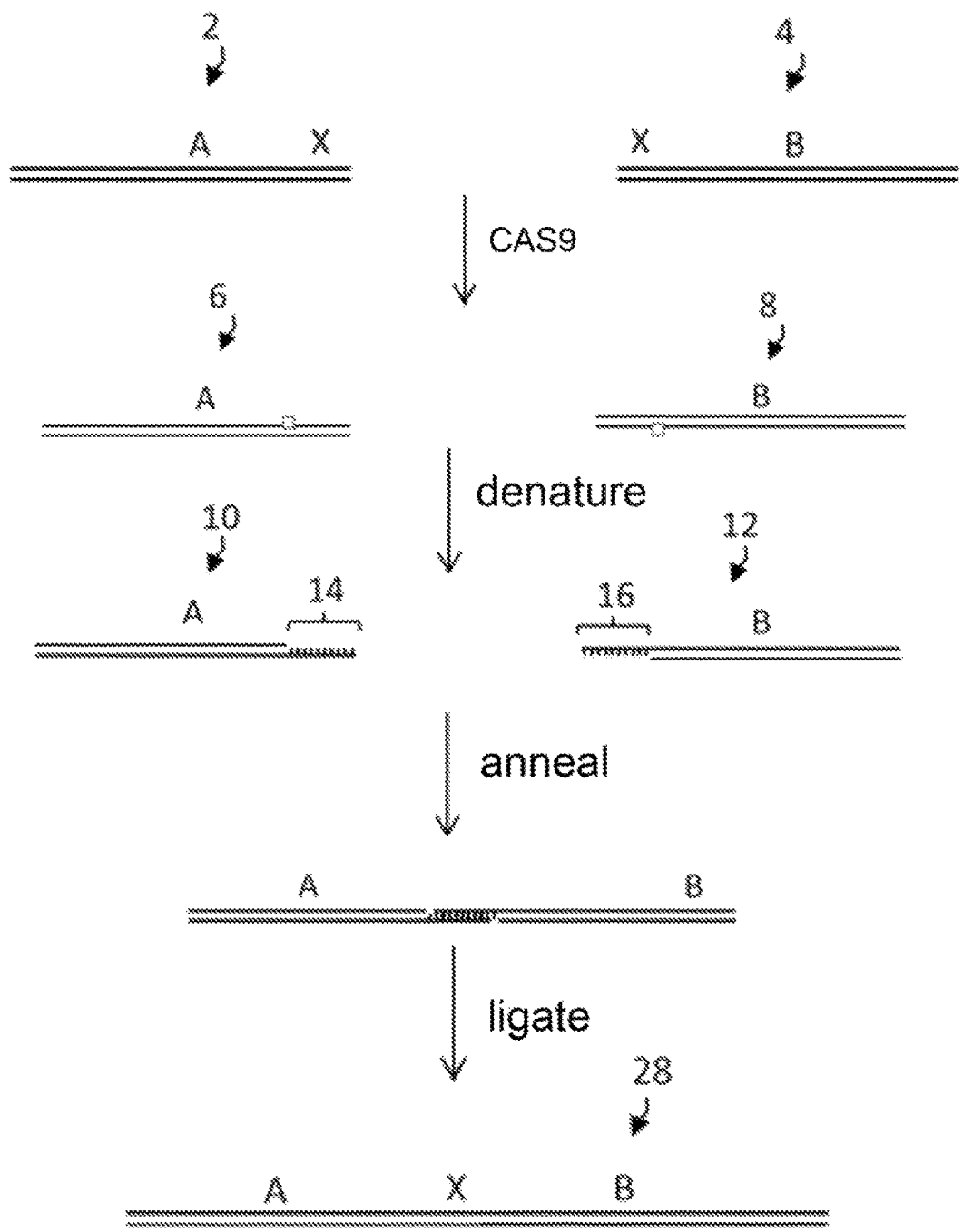
FIG. 1 schematically illustrates an embodiment of the present method.

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine, thymine, uracil (G, C, A, T and U respectively). DNA and RNA have a deoxyribose and ribose sugar backbone, respectively, whereas PNA's backbone is composed of repeating N-(2-aminoethyl)-glycine units linked by peptide bonds. In PNA various purine and pyrimidine bases are linked to the backbone by methylene carbonyl bonds. A locked nucleic acid (LNA), often referred to as inaccessible RNA, is a modified RNA nucleotide. The ribose moiety of an LNA nucleotide is modified with an extra bridge connecting the 2' oxygen and 4' carbon. The bridge "locks" the ribose in the 3'-endo (North) conformation, which is often found in the A-form duplexes. LNA nucleotides can be mixed with DNA or RNA residues in the oligonucleotide whenever desired. The term "unstructured nucleic acid", or "UNA", is a nucleic acid containing non-natural nucleotides that bind to each other with reduced stability. For example, an unstructured nucleic acid may contain a G' residue and a C' residue, where these residues correspond to non-naturally occurring forms, i.e., analogs, of G and C that base pair with each other with reduced stability, but retain an ability to base pair with naturally occurring C and G residues, respectively. Unstructured nucleic acid is described in US20050233340, which is incorporated by reference herein for disclosure of UNA.

The term "oligonucleotide" as used herein denotes a single-stranded multimer of nucleotide of from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

The terms "anneals" and "annealing" refers to a process in which a nucleic acid strand hybridizes to and forms a stable duplex, either a homoduplex or a heteroduplex, under normal hybridization conditions with a second complementary nucleic acid strand, and does not form a stable duplex with unrelated nucleic acid molecules under the same normal hybridization conditions. The formation of a duplex is accomplished by annealing two complementary nucleic acid strands in a hybridization reaction. The hybridization reaction can be made to be highly specific by adjustment of the hybridization conditions (often referred to as hybridization stringency) under which the hybridization reaction takes place, such that hybridization between two nucleic acid strands will not form a stable duplex, e.g., a duplex that retains a region of double-strandedness under normal stringency conditions, unless the two nucleic acid strands contain a certain number of nucleotides in specific sequences which are substantially or completely complementary. "Normal hybridization or normal stringency conditions" are readily determined for any given hybridization reaction. See, for example, Ausubel et al., Current Protocols in Molecular Biology, John Wiley & Sons, Inc., New York, or Sambrook et al., Molecular Cloning: A Laboratory Manual, Cold Spring Harbor Laboratory Press. As used herein, the term "hybridizing" or "hybridization" refers to any process by which a strand of nucleic acid binds with a complementary strand through base pairing.

A nucleic acid is considered to be "selectively hybridizable" to a reference nucleic acid sequence if the two sequences specifically hybridize to one another under moderate to high stringency hybridization and wash conditions. Moderate and high stringency hybridization conditions are known (see, e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). One example of high stringency conditions include hybridization at about 42 C in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C.

The term "duplex," or "duplexed," as used herein, describes two complementary polynucleotides that are base-paired, i.e., hybridized together.

The term "amplifying" as used herein refers to the process of synthesizing nucleic acid molecules that are complementary to one or both strands of a template nucleic acid. Amplifying a nucleic acid molecule typically includes denaturing the template nucleic acid, annealing primers to the template nucleic acid at a temperature that is below the melting temperatures of the primers, and enzymatically elongating from the primers to generate an amplification product. The denaturing, annealing and elongating steps each can be performed once. Generally, however, the denaturing, annealing and elongating steps are performed multiple times (e.g., at least 5 or 10 times, up to 30 or 40 or more times) such that the amount of amplification product is increasing, often times exponentially, although exponential amplification is not required by the present methods. Amplification typically requires the presence of deoxyribonucleoside triphosphates, a DNA polymerase enzyme and an appropriate buffer and/or co-factors for optimal activity of the polymerase enzyme. The term "amplification product" refers to the nucleic acid sequences, which are produced from the amplifying process as defined herein.

The term "free in solution," as used here, describes a molecule, such as a polynucleotide, that is not bound or tethered to another molecule.

The term "ligating", as used herein, refers to the enzymatically catalyzed joining of the terminal nucleotide at the 5' end of a first DNA molecule to the terminal nucleotide at the 3' end of a second DNA molecule.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

If two nucleic acids are "complementary", they hybridize with one another under high stringency conditions. The term "perfectly complementary" is used to describe a duplex in which each base of one of the nucleic acids base pairs with a complementary nucleotide in the other nucleic acid. In many cases, two sequences that are complementary have at least 10, e.g., at least 12 or 15 nucleotides of complementarity.

An "oligonucleotide binding site" refers to a site to which an oligonucleotide hybridizes in a target polynucleotide. If an oligonucleotide "provides" a binding site for a primer, then the primer may hybridize to that oligonucleotide or its complement.

The term "strand" as used herein refers to a nucleic acid made up of nucleotides covalently linked together by covalent bonds, e.g., phosphodiester bonds.

In a cell, DNA usually exists in a double-stranded form, and as such, has two complementary strands of nucleic acid referred to herein as the "top" and "bottom" strands. In certain cases, complementary strands of a chromosomal region may be referred to as "plus" and "minus" strands, the "first" and "second" strands, the "coding" and "noncoding" strands, the "Watson" and "Crick" strands or the "sense" and "antisense" strands. The assignment of a strand as being a top or bottom strand is arbitrary and does not imply any particular orientation, function or structure.

The term "denaturing," as used herein, refers to the separation of at least a portion of the base pairs of a nucleic acid duplex by placing the duplex in suitable denaturing conditions. Denaturing conditions are well known in the art. In one embodiment, in order to denature a nucleic acid duplex, the duplex may be exposed to a temperature that is above the Tm of the duplex, thereby releasing one strand of the duplex from the other. In certain embodiments, a nucleic acid may be denatured by exposing it to a temperature of at least 90° C. for a suitable amount of time (e.g., at least 30 seconds, up to 30 mins). In certain embodiments, fully denaturing conditions may be used to completely separate the base pairs of the duplex. In other embodiments, partially denaturing conditions (e.g., with a lower temperature than fully denaturing conditions) may be used to separate the base pairs of certain parts of the duplex (e.g., regions enriched for A-T base pairs may separate while regions enriched for G-C base pairs may remain paired). Nucleic acids may also be denatured chemically (e.g., using urea or NaOH).

The term, "intramolecularly ligating" refers to a ligation in which the 5' end and the 3' end of a strand of nucleic acid are ligated to one another to produce a circular DNA molecule.

The term "re-circularizing", as used herein, refers to the intramolecular ligation of a linearized molecule that was previously circular.

The term "synthon", as used herein, refers to a synthetic nucleic acid that has been assembled in vitro from other nucleic acids.

The term "immediately adjacent", as used herein, means operably linked. For example, two coding sequences are immediately adjacent to one another if they can be transcribed and translated into a protein in a cell. In certain cases, the term "immediately adjacent" means that there are no intervening nucleotides between two sequences.

The term "similar to one another" in the context of a polynucleotide or polypeptide, means sequences that are at least 70% identical, at least 80% identical, at least 90% identical, or at least 95% identical, to one another.

The term "polymerase chain assembly", as used herein, refers to a protocol in which multiple overlapping oligonucleotides are combined and subjected to multiple rounds of primer extension (i.e., multiple successive cycles of primer extension, denaturation and renaturation in the presence of a polymerase and nucleotides) to extend the oligonucleotides using each other as a template, thereby producing a product molecule. In many cases, the final product molecule is amplified using primers that bind to sites at the ends of the product molecule, and the product molecule is digested with one or more restriction enzymes and cloned. Polymerase chain assembly may include additional steps, such as digestion of the product molecule with a restriction enzyme to, e.g., prepare the product molecule for cloning.

The term "double-stranded DNA molecule" refers to a DNA duplex. The ends of such a molecule may be a defined or undefined sequence.

The term "target sequence" refers to a sequence in a double-stranded DNA molecule, where the sequence is targeted for nicking by Cas9. In many cases, a target sequence may be unique in any one starting molecule and, as will be described in greater detail below, multiple different starting molecules may contain the same target sequence. Any one starting molecule can contain multiple target sequences, where the multiple target sequences are different from one another, or their complements.

The term "nicking", as used herein, refers to a reaction that breaks the phosphodiester bond between two nucleotides in one strand of a double-stranded DNA molecule to produce a 3' hydroxyl group and a 5' phosphate group.

The term "nick site," as used herein, refers to the site at which a double-stranded DNA molecule has been nicked.

The term "complementary overhangs" refers to overhangs that can anneal together in a way that provides for ligatable junctions (i.e., a double stranded DNA molecule that contains one or more nicks).

The term "Cas9 enzyme" refers to a complex comprising a Cas9 protein and a guide RNA (gRNA). The guide RNA may be composed of two molecules, i.e., one crRNA, which hybridizes to a target and provides sequence specificity, and one tracrRNA, which is hybridized to the crRNA and required for catalytic activity. As is well known, the guide RNA may be a single molecule (i.e., a sgRNA) that contains crRNA and tracrRNA sequences. A Cas9 protein may be at least 80% identical (e.g., at least 90% identical, at least 95% identical or at least 98% identical or at least 99% identical) to a wild type Cas9 protein, e.g., to the *Streptococcus pyogenes* Cas9 protein.

For Cas9 to successfully bind to DNA, the target sequence in the genomic DNA should be complementary to the gRNA sequence and must be immediately followed by the correct protospacer adjacent motif or "PAM" sequence. The PAM sequence is present in the DNA target sequence but not in the gRNA sequence. Any DNA sequence with the correct target sequence followed by the PAM sequence will be bound by Cas9. The PAM sequence varies by the species of the bacteria from which Cas9 was derived. The most widely used Type II CRISPR system is derived from *S. pyogenes* and the PAM sequence is NGG located on the immediate 3' end of the gRNA recognition sequence. The PAM sequences of Type II CRISPR systems from exemplary bacterial species include: *Streptococcus pyogenes* (NGG), *Neisseria*

*meningitidis* (NNNNGATT), *Streptococcus thermophilus* (NNAGAA) and *Treponema denticola* (NAAAAC).

The term "Cas9 nickase enzyme" refers to a modified version of the Cas9 enzyme, as described above, containing a single inactive catalytic domain, either RuvC- or HNH-. With only one active nuclease domain, the Cas9 nickase cuts only one strand of the target DNA, creating a single-strand break or "nick". A Cas9 nickase is still able to bind DNA based on gRNA specificity, though nickases will only cut one of the DNA strands. The majority of CRISPR plasmids currently being used are derived from *S. pyogenes* and the RuvC domain can be inactivated by an amino acid substitution at position D10 (e.g., D10A) and the HNH domain can be inactivated by an by an amino acid substitution at position H840 (e.g., H840A), or at positions corresponding to those amino acids in other proteins. As is known, the D10 and H840 variants of Cas9 cleave a Cas9-induced bubble at specific sites on opposite strands of the DNA within the bubble. Depending on which mutant is used, the guide RNA-hybridized strand or the non-hybridized strand may be cleaved. Thus, one CAS9 nickase (e.g., the D10 or H840 variant) can be used to create a 3' overhang and the other nickase can be used to create a 5' overhang at the same locus by cleaving the opposite strand of DNA.

The term "spaced apart" refers to nicks that are on different strands of DNA that are separated by a certain number of base paired nucleotides.

The term "corresponding positions" refers to the same positions in a sequence if the sequences are aligned with one another.

The term "moderately denaturing conditions" are denaturing conditions that allow a duplex of 10-30 base pairs (e.g., duplex of 15-25 or 18-23 base pairs) to denature, leaving a duplex of at least twice or at least three times that length, e.g., a duplex of at least 20 base pairs, a duplex of at least 30 base pairs, a duplex of at least 50 base pairs, a duplex of at least 100 base pairs or a duplex of at least 200 base pairs) annealed. Depending on the length of the duplex that one wishes to denature, moderately denaturing conditions may include incubation at a temperature in the range of 60° C. to 90° C., e.g., 60° C. to 80° C. or 60° C. to 70° C. for a certain time, e.g., a time in the range of 30 s to 5 min, followed by an optional rapid cooling to, e.g., 4° C. The conditions for each procedure can be readily optimized.

The following description explains the formulas used in this disclosure. Certain polynucleotides described herein may be referred by a formula (e.g., formula A-X-B). The components of the formula, e.g., "A," "X" and "B" refer to separately definable sequences of nucleotides within a polynucleotide, where the sequences are linked together covalently such that a polynucleotide described by a formula is a single molecule. The components of the formula may be immediately adjacent to one another or spaced from one another in the single molecule. In certain cases, other sequence elements, e.g., other primer binding sites, molecular barcodes, promoters, etc. may be provided by sequences that are between the components of a formula. Further, each of the various components of a formula may have functions in addition to those described herein. Unless otherwise indicated or implicit from the context, a polynucleotide defined by a formula may have additional sequence at its 3' end, its 5' end or both the 3' and 5' ends.

The term "complementary" refers to a level of complementarity at which two sequences can specifically hybridize to one another under the conditions used. Two complementary sequences may have, for example, 1, 2, 3, or 4 mismatches. In certain cases, two complementary sequences may have no mismatches, i.e., may be perfectly complementary to each other.

As would be understood, reference to a "junction" refers to the phosphodiester bond that joins two sequences.

Figure 6:
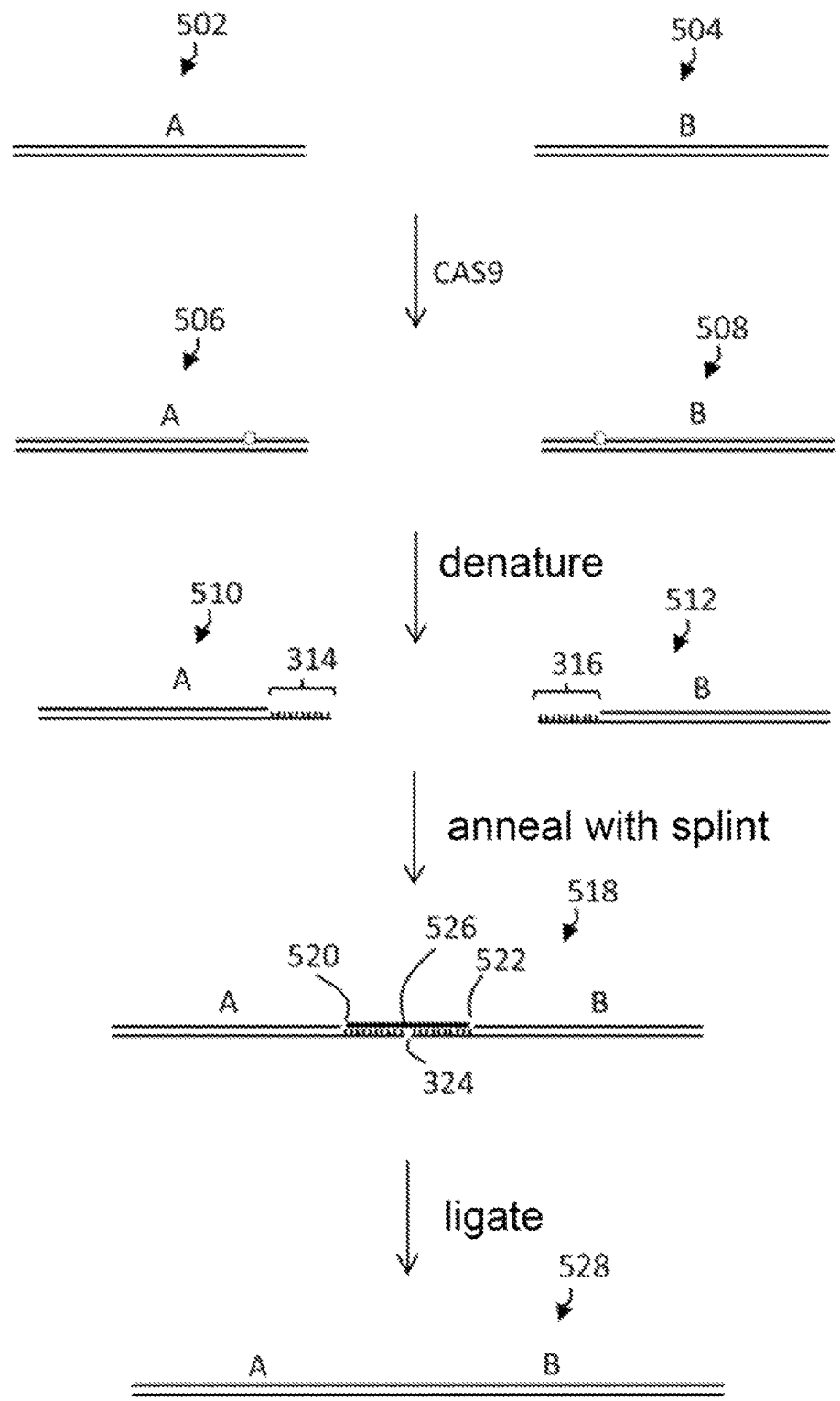
FIG. 6 schematically illustrates an alternative embodiment of the present method.

The term "splint oligonucleotide", as used herein, refers to an oligonucleotide that, when hybridized to other polynucleotides, acts as a "splint" to position the polynucleotides next to one another so that the bottom strands of the polynucleotides can be ligated together and the top strands of polynucleotides can be ligated to the splint, as illustrated in FIG. 6.

The term "common sequence", as used herein, is intended to refer to a sequence of nucleotides that is the same in two molecules.

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

As noted above, a method comprising (a) providing two double-stranded DNA molecules with a common sequence, wherein the common sequence is at the end of each molecule; (b) nicking one strand in the common sequence of both molecules at a respective nicked site; (c) moderately denaturing both molecules to remove a single-stranded fragment from the nicked site to one end of each molecule, wherein the single-stranded fragment includes the common sequence in part or in whole, resulting in an overhanging sequence in each molecule, and the overhanging sequences in both molecules are complementary to each other; (d) allowing the overhanging sequences of both molecules to anneal to each other, and ligating the molecules.

An exemplary implementation of this method is shown I FIG. 1. In certain embodiments, the method comprises: (a) obtaining two double-stranded DNA molecules, e.g., a first double-stranded DNA molecule 2 of formula A-X and a second double-stranded DNA molecule 4 of formula X-B, wherein X is a common sequence of 4 to 30 base pairs (e.g., 18-23) in length that is the same in both molecules. The next step includes nicking one strand in the common sequence of both molecules at a respective nicked site. As shown, this step may involve: (i) nicking the junction of A and X in the top strand of first molecule of double-stranded DNA using Cas9 nickase and a first guide RNA; and (ii) nicking the junction of X and B in the bottom strand of the second molecule of double-stranded DNA, using Cas9 nickase and a second guide RNA. As shown in FIG. 1, this results in nicked molecules 6 and 8, each having a nick on opposite strands in target sequence X. Next, nicked molecules 6 and 8 are denatured in moderately denaturing conditions, thereby producing double-stranded products 10 and 12 that comprise complementary overhangs 14 and 16 in range of 4-30 bases in length. Next, the method comprises allowing the overhanging sequences of both molecules to anneal to each other, and ligating the molecules. As shown, this step may comprise ligating the double-stranded products 10 and 12 together by annealing the overhangs to one another and ligating the ends of the products together using a ligase to yield recombinant product molecule 28. As shown, recombinant product molecule 28 is of formula A-X-B.

Figure 2:
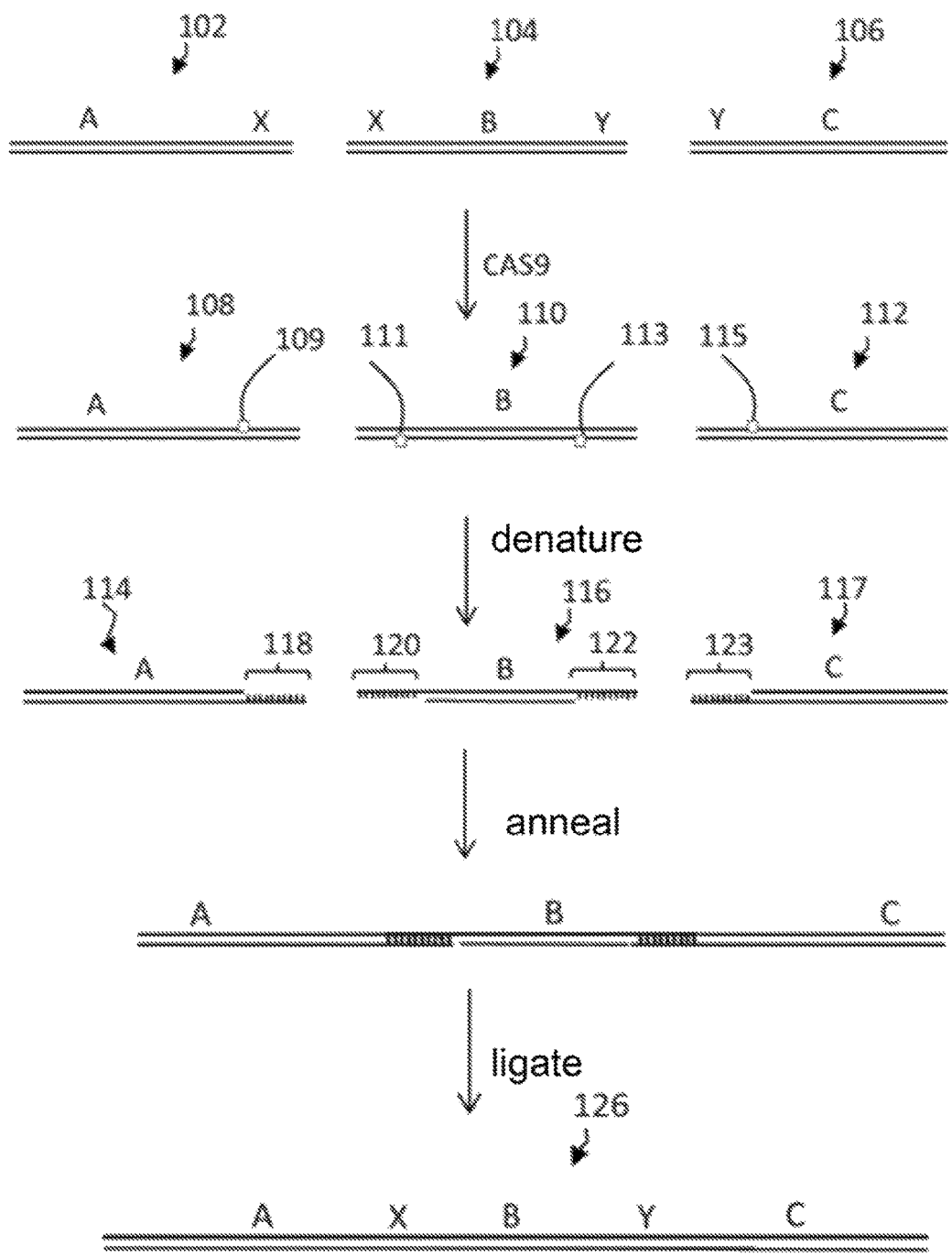
FIG. 2 schematically illustrates an embodiment of the present method.

As shown in FIG. 2, the principle of the method shown in FIG. 1 can be used to join several double-stranded DNA molecule in an end-to end fashion. With reference to FIG. 2, this method may comprise: (a) obtaining a first double-stranded DNA molecule 102 of formula A-X, a second double-stranded DNA molecule 104 of formula X-B-Y and a third double-stranded DNA molecule 106 of formula Y-C, wherein X and Y are different target sequences of 4-30 base pairs in length. The next step of the method includes: (b) nicking: (i) the junction of A and X in the first double-stranded DNA molecule using Cas9 nickase and a first guide RNA, resulting in product 108 that contains nick 109; (ii) the junction of X and B and the junction of B and Y in in the second double-stranded DNA molecule, using the Cas9 nickase and a second and third guide RNAs, resulting in product 110 that contains nicks 111 and 113, respectively; and (iii) the junction between Y and C in the third double-stranded DNA molecule, using the Cas9 nickase and a fourth guide RNA, resulting in product 112 that contains nick 115. In the next step of the method, the products 109, 110 and 112 are denatured in moderately denaturing conditions, thereby producing double-stranded products 114, 116 and 117 that comprise complementary overhangs 118, 120, 122 and 123 that are in range of 4-30 bases in length. The next step of this method involves (d) ligating the double-stranded products 114, 116 and 117 to one another by annealing the overhangs to one another and ligating the ends of the products together using a ligase, thereby joining the double-stranded products together and producing a product molecule 126 of the formula A-X-B-Y-C.

The principle of the method shown in FIG. 1 can also be used to recombine sequence is a combinatorial manner. For example, double-stranded DNA molecules formulas A-X, B-X, X-C and X-D can be nicked in target sequence X and subjected to partial denaturation to produce products that contain complementary overhangs. Then, overhangs can be annealed and the ends of the products can be ligated together to produce products of formulas A-X-C, A-X-D, B-X-C and B-X-D.

Figure 3:
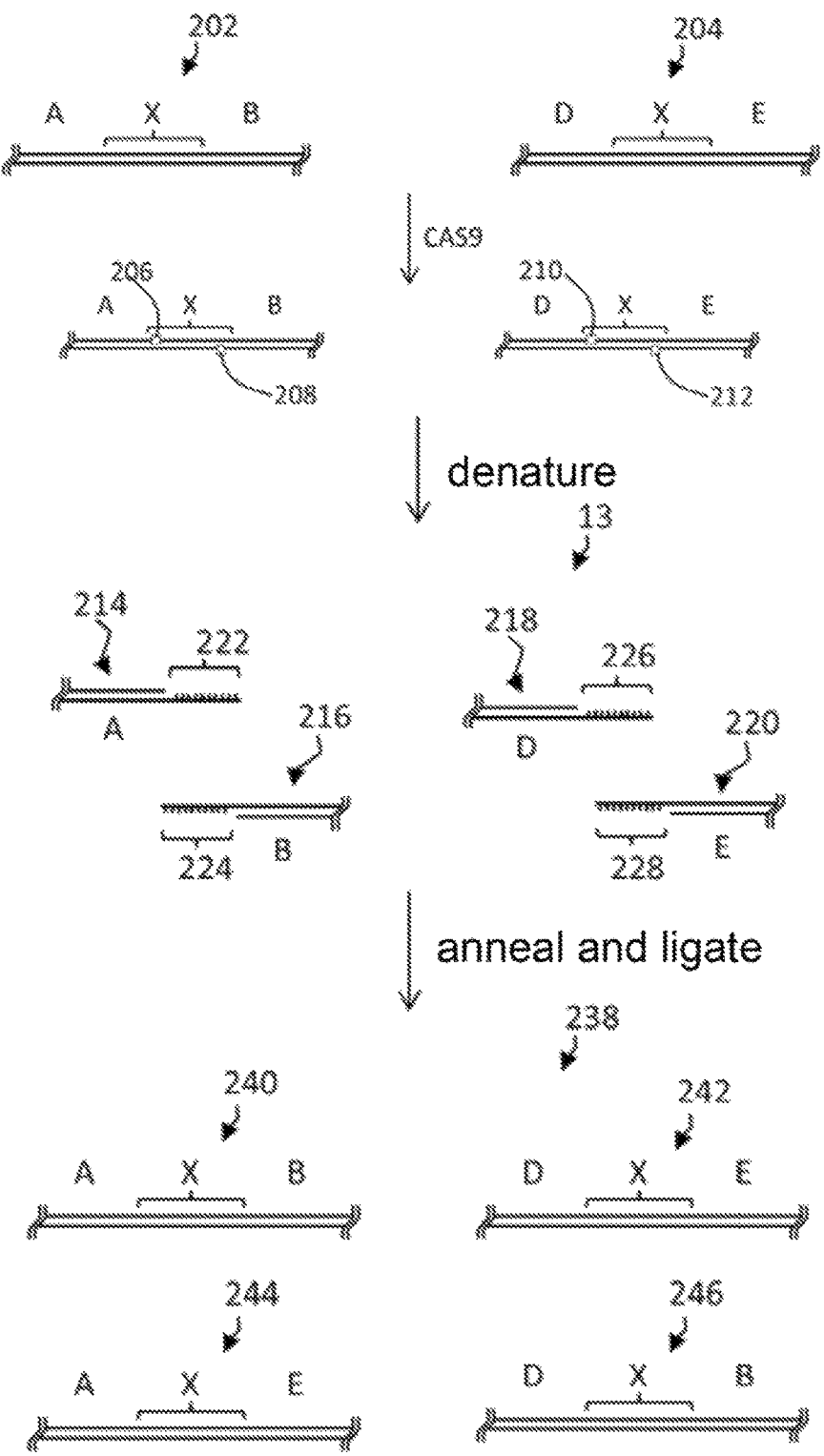
FIG. 3 schematically illustrates one embodiment of the present method.

A further method for recombining DNA molecules is provided. With reference to FIG. 3, the first step of method may involve obtaining a first double-stranded DNA molecule 202 of formula A-X-B and a second double-stranded DNA molecule 204 of formula D-X-E, where X is a target sequence of 4-30 base pairs in length that is the same in both molecules. The next step includes nicking the junctions of target sequence X in the first and second DNA molecules 202 and 204 using a Cas9 nickase. As shown, nicks 206 and 208 are spaced apart by 4 to 30 bases (e.g., 15 to 25 or 18 to 23 bases) and nicks 210 and 212 are at corresponding positions in the first and second DNA molecules (which means that the sequence between the nicks in the nicked product molecules are the same. The next step includes denaturing the nicked products under moderately denaturing conditions. In this step, denaturing conditions are sufficient to denature the base pairing between the nick sites, but not the rest of the nicked molecules, thereby producing double-stranded products 213 that comprise complementary overhangs that are of 4 to 30 bases in length (e.g., 15 to 25 or 18 to 23 bases). In the embodiment shown, denaturation results in four products, 214, 216, 218 and 220, each of which contains an overhang (222, 224, 226, and 228). As shown, overhang 222 is complementary to overhangs 224 and 228, and overhang 26 is complementary to overhangs 224 and 228. Next, the method comprises ligating the double-stranded products 213 together by annealing the overhangs to one another and joining the ends of the products together using a ligase to produce recombinant product molecules 238. As shown, recombinant product molecules 238 comprises molecule 240 (which is the same as molecule 2), 242 (which is the same as molecule 4), molecule 244 of formula A-X-E molecule 246 of formula D-X-B.

The principles of the method illustrated in FIG. 3 can be used to recombine several double stranded DNA molecules to provide recombinant product molecules that contain different combinations of sequences from the starting molecules. In these embodiments, in theory, if the number of different starting molecules is n and there is only one target sequence then the number of product molecules can be has high as $n^2$ (although, in practice, the actually number of product molecules may be less than $n^2$).

Figure 4:
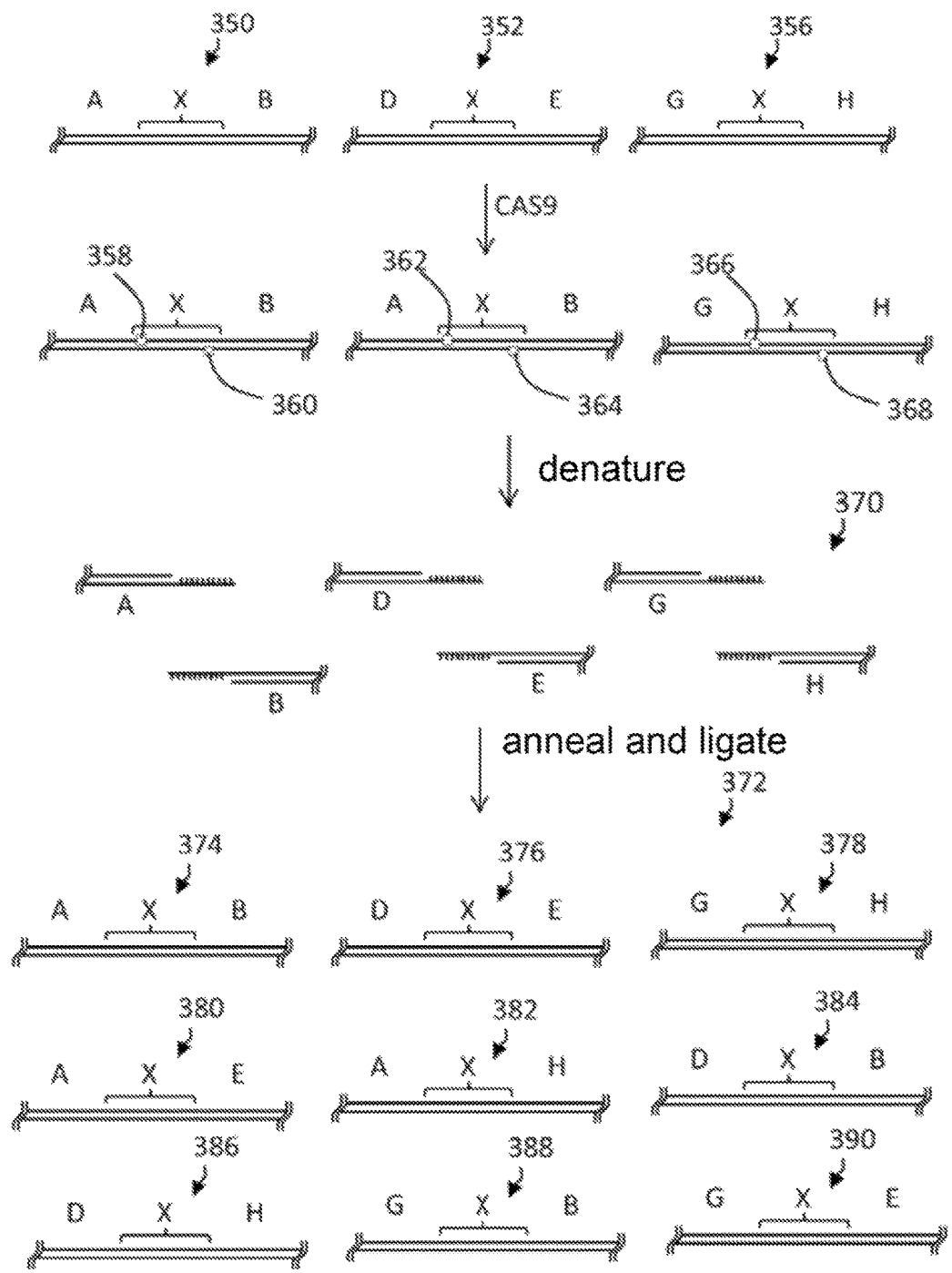
FIG. 4 schematically illustrates another embodiment of the present method.

An example of this embodiment is shown in FIG. 4. With reference to FIG. 4, the method may comprise obtaining a first double-stranded DNA molecule 350 of formula A-X-B, a second double-stranded DNA molecule 352 of formula D-X-E, and a third double stranded DNA molecule 356 of formula G-X-H. As shown, the method comprises nicking both strands of target sequence X in the first, second and third DNA molecules using a Cas9 nickase, as described above, where, in any one molecule, the nicks are spaced apart by 4-30 bases and are at corresponding positions in the first, second and third DNA molecules. As shown, 358, 362 and 366 are at the same site in sequence X, and that site is 4 to 30 bases from the other nick site in the molecule (nick sites 360, 364 and 368). Next, the nicked products are denatured under moderately denaturing conditions as described above to produce double-stranded products 70 that comprise complementary overhangs that are of 4 to 30 bases in length. Next, the method comprises ligating the double-stranded products together by annealing the overhangs to one another and ligating the ends of the products together using a ligase. In this example, the resulting recombinant product molecules 72 comprises molecules of formula A-X-B (374), D-X-E (376), and G-X-H (378), which are the same as molecules 350, 352 and 356, as well as recombed molecules of formula A-X-E (380), A-X-H (382), D-X-B (384), D-X-H (386), G-X-B (388) and G-X-E (390). The principle of this method can be expanded to a recombine a greater number of initial double stranded DNA molecules (e.g., 3, 4, 5, up to 10, up to 50, up to 100, or up to 1000 or more double stranded DNA molecules).

Figure 5:
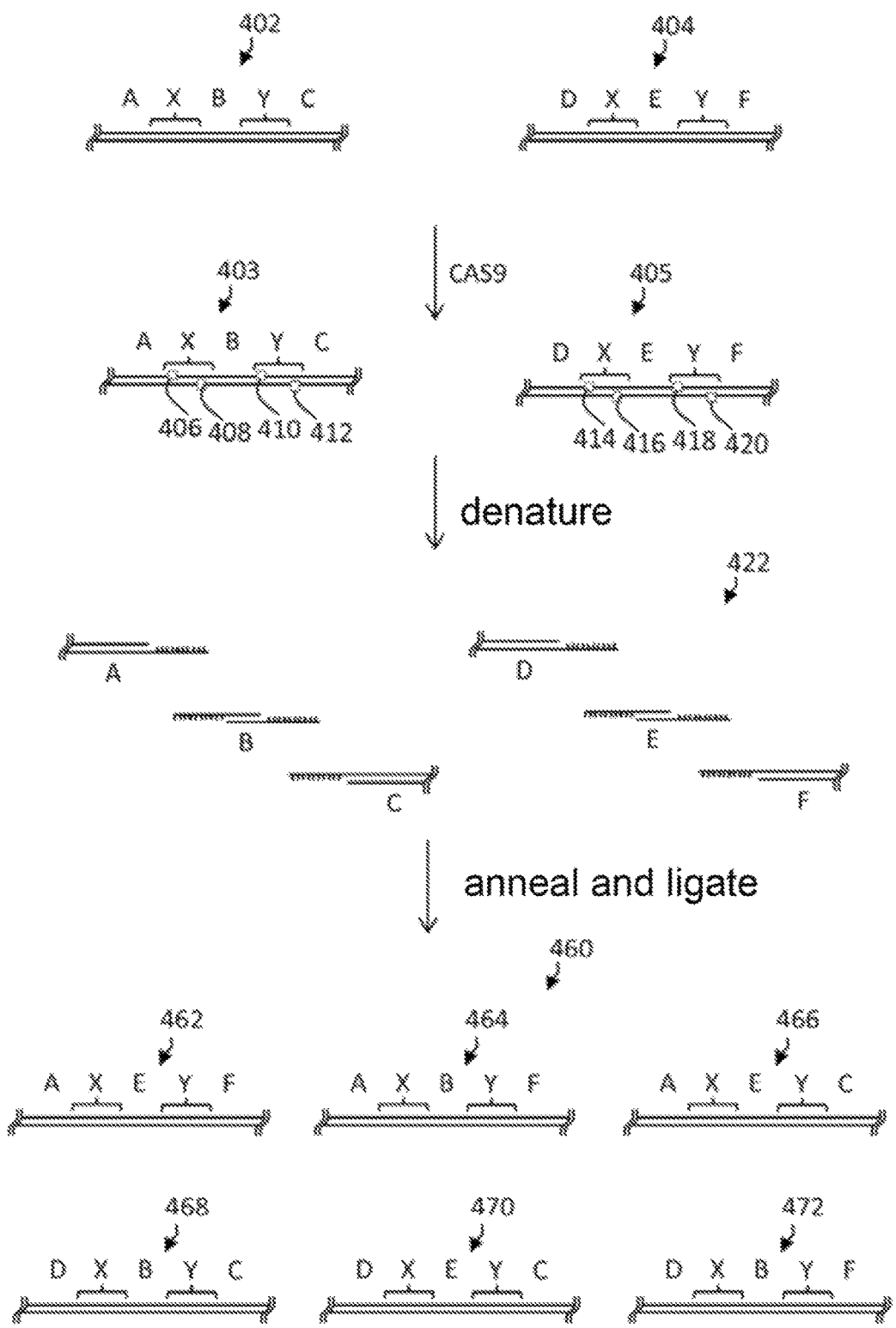
FIG. 5 schematically illustrates a further embodiment of the present method.

The principles of the method illustrated in FIG. 3 can also be used to recombine several double stranded DNA molecules in an end-to-end manner to provide recombinant product molecules that contain different combinations of sequences from the starting molecules. This method is illustrated in FIG. 5. With reference to FIG. 5, this embodiment of the method may comprise obtaining a first double-stranded DNA molecule 402 of the formula A-X-B-Y-C and a second double-stranded DNA molecules 404 of the formula D-X-E-Y-F, wherein X and Y are different target sequences of 4-30 base pairs in length, as described above) and do not hybridize to one another. This embodiment of the method involves nicking the junctions of X and Y of the first, second, and third DNA molecules using a Cas9 nickase, wherein the nicks are spaced apart by 4-30 bases and are at corresponding positions in the first, second and third DNA molecules. Nicked product 403 has four nicks 406, 408, 410 and 412 (two in X and two in Y) and nicked product 405 has four nicks 414, 416, 418 and 420 (two in X and two in Y), as described above. Next, the method comprises denaturing the nicked products 403 and 405 under moderately denaturing conditions, as described above, to produce double-stranded products 422 that comprise complementary overhangs of 4 to 30 bases. Next, the method comprises ligating the double-stranded products together by annealing the overhangs to one another and ligating the ends of the products together using a ligase. In this example, the resulting recombinant product molecules 460 comprises molecules of formula A-X-B-Y-C and D-X-E-Y-F, which are the same as molecules 402 and 404 and not shown in FIG. 5, as well as product molecules of the formula A-X-E-Y-F (462), A-X-B-Y-F (464), A-X-E-Y-C (466), D-X-B-Y-C (468), D-X-E-Y-C (470), and D-X-B-Y-F (472).

The principle of any of the methods described above can be expanded to recombine a greater number of initial double stranded DNA molecules (e.g., 3, 4, 5, up to 10, up to 50, up to 100, or up to 1000 or more double stranded DNA molecules), end to end in certain cases in a combinatorial manner.

An alternative method that can be used separately or in conjunction with the method described above is illustrated in FIG. 6. All of the principles and utilities described above may be applied to the method described below.

With reference to FIG. 6, this method comprises: obtaining a first double-stranded DNA molecule 502 of formula A and a second double-stranded DNA molecule 504 of formula B. In this embodiment, the method comprises nicking: (i) the first fragment of double-stranded DNA at a site that is 4-30 bases from the 3' end of one of the strands of the first fragment, using Cas9 nickase and a first guide RNA; and (ii) the second fragment of double-stranded DNA at a site that is 4-30 bases from the 5' end of one of the strands of the second fragment, using Cas9 nickase and a second guide RNA. This step of the method results in nicked products 506 and 508. Next, the nicked products 506 and 508 are denatured under moderately denaturing conditions, as described above, thereby producing double-stranded products 510 and 512 that comprise overhangs 514 and 516, respectively, that are in range of 4 to 30 bases in length. In this case, the overhangs are not complementary to one another and the double-stranded products 510 and 512 are then ligated together by annealing the overhangs to a splint oligonucleotide 526 to produce molecule 518 that contains nicks 520, 522 and 524, and then joining the double-stranded products to the splint oligonucleotide by ligation and producing a product molecule 528 of the formula A-B. The length of the splint oligonucleotide depends on the length of the overhangs. In some embodiments, the splint oligonucleotide may be from 20 to 60 bases in length.

As with the first method described above, this alternative method may be used to recombine several double stranded DNA molecules to provide recombinant product molecules that contain different combinations of sequences from the starting molecules. In these embodiments, in theory, if the number of different starting molecules is n, then the number of product molecules can be has high as $n^2$ (although, in practice, the actually number of product molecules may be less than this number).

Figure 7:
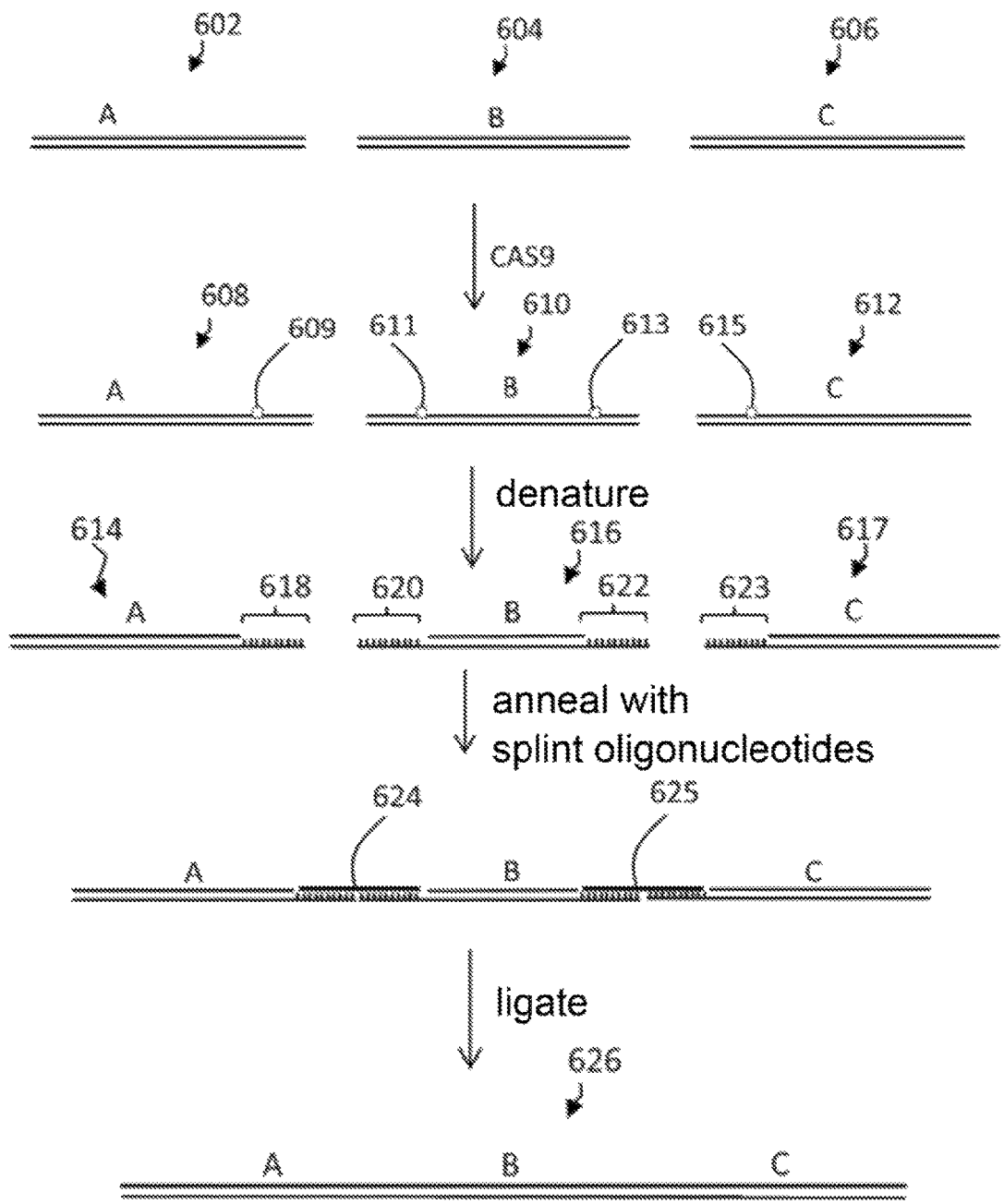
FIG. 7 schematically illustrates an alternative embodiment of the present method.

This alternative method can also be used to recombine several double stranded DNA molecules in an end-to-end manner to provide recombinant product molecules that contain different combinations of sequences from the starting molecules. This embodiment is illustrated in FIG. 7. With reference to FIG. 7, this embodiment may comprise (a) obtaining a first double-stranded DNA molecule 602 of formula A, a second double-stranded DNA molecule 604 of formula B and a third double-stranded DNA molecule 606 of formula C. Next, the method comprises: (b) nicking: (i) the first double-stranded DNA molecule at a site that is 4 to 30 bases from an end of one of the strands of the first fragment, using Cas9 nickase and a first guide RNA, to produce nicked product 608 that comprises nick 609; (ii) each end of the second double-stranded DNA molecule, at sites that are 4 to 30 bases away from a 3' or 5' terminus, using the Cas9 nickase and a second and third guide RNAs, to produce nicked product 610 that comprises nicks 611 and 613; (iii) the third double-stranded DNA molecule at a site that is 4 to 30 bases from an end of one of the strands of the third fragment, using the Cas9 nickase and a fourth guide RNA, to produce nicked product 612 that comprises nick 615. Next, the nicked products 608, 610 and 612 are denatured under moderately denaturing conditions, thereby producing double-stranded products 614, 616 and 617 that comprise overhangs 618, 620, 622 and 623 that are each in range of 4 to 30 bases in length. As noted above, the overhangs in this method are not complementary to one another and they are ligated by annealing the overhangs to a first splint oligonucleotide 624 and a second splint oligonucleotide 625 and ligating the ends of the products together using a a ligase. As shown, the first splint oligonucleotide 624 hybridizes to overhangs from products 614 and 616, and the second splint oligonucleotide 625 hybridizes to overhangs from products 616 and 617. As shown products 614, 616 and 617 ligate to splint oligonucleotides 624 and 625 to produce a product molecule 626 of formula A-B-C.

As would be apparent, the initial double stranded DNA molecules may be of any length (e.g., 50 bp to 2 kb in length or 100 bp to 1 kb, or longer). In some cases, the first and second molecules are each of at least 100 bp in length. In some embodiments, the different molecules may be of different lengths. Sequence A, B, D and E may be different sequences of any length (e.g., 10 bp to 1 kb or longer). In some cases, the sequences in corresponding positions in different molecules (e.g., A and D or B and E) may be at least 80% identical to one another (e.g., at least 90% or at least 95% identical to one another). In such cases, the sequences in corresponding positions in different molecules may be variants of the same sequence.

In these embodiments, the splint may be added in a stoichiometric excess relative to the DNA molecules to favor formation of products while disfavoring reformation of the starting molecules.

The initial double stranded molecules can be from any suitable source. In certain cases, double stranded molecules can be double stranded oligonucleotides (i.e., two complementary single stranded oligonucleotides that have been annealed to one another), or alternatively, they can be PCR products. In certain cases, the initial double stranded DNA molecules may be synthons that have been made by other means, e.g., by polymerase chain assembly. Double stranded molecules may be circular or linear, depending on how the method is performed.

The different sequences of the initial double stranded molecules (e.g., A, B, D, E, etc.) can be any suitable sequence. In particular cases, the sequences may encode different parts of a single protein such that, after the sequences have recombined, the coding sequences are fused in frame to encode a longer coding sequence that encodes the protein. In other embodiments, the sequences may be different domains of a protein, different proteins, different parts of a plasmid (e.g. promoters, terminators, resistance markers, backbones, origins of replication, expression cassettes, secretion signals, etc.).

In any embodiment described herein, the sequences that are denatured by moderate denaturation may be removed so that they do no interfere with subsequent reactions. In some cases, because the sequences are relatively short and single stranded, they may be removed by size exclusion or by using a matrix that has affinity for either double stranded DNA or single stranded DNA, but not both. In other embodiments, the sequences may be removed or digested enzymatically.

Also as would be apparent, the guide RNA of the Cas9 nickase should be designed so as to bind to an appropriate sequence in the initial double stranded molecules, and the initial double stranded molecules should contain a PAM sequence that has a sequence and position appropriate for the Cas9 protein being used. In some embodiments (and as shown in FIG. 8) the guide RNA may bind to a site sequence X, and sequence X may contain the CCN trinucleotide required by the *Streptococcus pyogenes* Cas9 protein. As shown, the Cas9 enzyme may nick at a site that is immediately 3' of the CCN trinucleotide. In the embodiment shown in FIGS. 3 and 7, the method may be done using a single Cas9 protein and two guide RNAs (one for each nick). In some embodiments, the guide RNAs are complementary to opposite strands of the target sequence (i.e., one guide binds to the top strand and the other guide RNA binds to the bottom strand).

In certain cases, one or more of the initial double stranded DNA molecules may have PCR primer sites so that the final products can be amplified by PCR and, optionally, cloned into a vector. If desired, the method can be used to produce a circular product, e.g., a plasmid or the like.

In some embodiments, the ligase used may be a thermostable ligase. In these embodiments, the method may comprise repeating steps (c) and (d) multiple times in succession, thereby allowing the reaction to cycle through multiple rounds of denaturation, annealing and ligation which should push the reaction to completion. In some embodiments, steps (b) to (d) (i.e., the nicking, denaturing and ligating steps) can be done in a single vessel and no additional reagents are added between those steps.

In certain embodiments, the method may further comprise cloning the product molecules into a vector. This may be done in a variety of different ways. In one embodiment, the ends of the product molecules may comprise a restriction site, and the cloning is done by digesting the product molecules using a restriction enzyme that cleaves at the restriction site to produce a clonable fragment; and ligating the products into a plasmid vector.

In other embodiments, the cloning may be done by amplifying the product molecules by PCR using PCR primers that bind to terminal sequences and cloning the amplified products into a plasmid vector. As would be understood, the PCR product may itself be digested by a restriction enzyme to facilitate cloning.

The product molecules can be of any sequence and, in certain cases, may encode a sequence of amino acids, i.e., may be a coding sequence. In other embodiments, the product molecules can be a regulatory sequence such as a promoter or enhancer. In particular cases, the product molecules may encode a regulatory RNA. In certain cases a product molecule may have a biological or structural function.

In particular cases, vector may be an expression vector designed for expression of the product molecules. In these embodiments, the expression vector may contain a promoter, terminator and other necessary regulatory elements to effect transcription and in certain cases translation of the product molecules, either as a single protein, or as a fusion with another protein. In these embodiments, the method may further comprise transferring the expression vector into a cell to produce the expression product (e.g., a protein) encoded by the product molecules. This embodiment of the method may comprise screening the expression product for an activity.

As noted above, in certain embodiments, three, four, five or six or more initial nucleic acids can be joined together and circularized using this method.

The above-described methods can be used in a variety of gene synthesis applications. Certain embodiments may be used to assemble several recombinant nucleic acids in the same reaction vessel. For example, certain embodiments may be used to assemble at least 2, at least 5, at least 10, at least 50, at least 100, at least 500, at least 1,000 or more synthons in the same reaction vessel. The embodiment described may be particularly useful for assembling, in the same reaction vessel, several variants of the same sequence, where the sequences of the variants are similar to one another.

Kits

Also provided by this disclosure is a kit for practicing the subject method, as described above. A subject kit may contain at least: (i) double stranded DNA molecules or primers for amplifying the same, as described above, (ii) a Cas9 nickase comprising guide RNAs that direct the Cas9 nickase to the appropriate cleavage sequences, as described above, and (iii) a DNA ligase, which may be thermostable. The various components of the kit may be present in separate containers or certain compatible components may be pre-combined into a single container, as desired.

In addition to the above-mentioned components, the subject kits may further include instructions for using the components of the kit to practice the subject methods, i.e., to provide instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging), etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

EXEMPLARY EMBODIMENTS

Some embodiments of the method comprise: (a) obtaining a first double-stranded DNA molecule of formula A-X and a second double-stranded DNA molecule of formula X-B, wherein X is a target sequence of 4 to 30 base pairs in length that is the same in both molecules; (b) nicking: (i) the junction between A and X in the first molecule of double-stranded DNA using Cas9 nickase and a first guide RNA; and (ii) the junction between X and B in the second molecule of double-stranded DNA using Cas9 nickase and a second guide RNA; (c) denaturing the nicked products of (b) in moderately denaturing conditions, thereby producing double-stranded products that comprise complementary overhangs in range of 4-30 bases in length; and (d) ligating the double-stranded products of (c) by annealing the complementary overhangs to one another and ligating the ends of the products together using a ligase, thereby joining the double-stranded products and producing a product molecule of the formula A-X-B.

These embodiments may comprise: (a) obtaining a first double-stranded DNA molecule of formula A-X, a second double-stranded DNA molecule of formula X-B-Y and a third double-stranded DNA molecule of formula Y-C, wherein X and Y are different target sequences of 4 to 30 base pairs in length; (b) nicking: (i) the junction between A and X in the first double-stranded DNA molecule using Cas9 nickase and a first guide RNA; (ii) the junction between X and B, and the junction between B and Y in the second double-stranded DNA molecule using the Cas9 nickase and a second and third guide RNAs; (iii) the junction between Y and C, in the third double-stranded DNA molecule using the Cas9 nickase and a fourth guide RNA; (c) denaturing the nicked products of (b) in moderately denaturing conditions, thereby producing double-stranded products that comprise complementary overhangs in range of 4-30 bases in length; and (d) ligating the double-stranded products of (c) by annealing the complementary overhangs to one another and ligating the ends of the products together using a ligase, thereby joining the double-stranded products together and producing a product molecule of the formula A-X-B-Y-C.

Some embodiments of the method may comprises: (a) obtaining a first double-stranded DNA molecule of formula A-X-B and a second double-stranded DNA molecule of formula D-X-E, wherein X is a target sequence of 4-30 base pairs in length that is the same in both molecules; (b) nicking the junctions between A and X, X and B, D and X, X and E in the first and second DNA molecules using a Cas9 nickase; (c) denaturing the nicked products of (b) under moderately denaturing conditions to produce double-stranded products that comprise complementary overhangs that are of 4-30 bases in length; and (d) ligating the double-stranded products of (c) by annealing the complementary overhangs to one another and ligating the ends of the products together using a ligase, thereby producing recombinant product molecules that comprise molecules of formula A-X-E and D-X-B.

These embodiments may comprise: (a) obtaining a first double-stranded DNA molecule of formula A-X-B, a second double-stranded DNA molecule of formula D-X-E, and a third double stranded DNA molecule of formula G-X-H; (b) nicking the junctions of X in the first, second and third DNA molecules using a Cas9 nickase; (c) denaturing the nicked products of (b) under moderately denaturing conditions to produce double-stranded products that comprise complementary overhangs that are of 4-30 bases in length; and (d) ligating the double-stranded products of (c) by annealing the complementary overhangs to one another and ligating the ends of the products together using a ligase, thereby producing recombinant product molecules that comprise molecules of formula A-X-E, A-X-H, D-X-B, D-X-H, G-X-B and G-X-E.

These embodiments may comprise: (a) obtaining a first double-stranded DNA molecule of the formula A-X-B-Y-C and a second double-stranded DNA molecules of the formula D-X-E-Y-F, wherein X and Y are different target sequences of at least 4-30 base pairs in length and do not hybridize to one another; (b) nicking the junctions of target sequences X and Y of the first and second DNA molecules using a Cas9 nickase; (c) denaturing the nicked products of (b) under moderately denaturing conditions to produce double-stranded products that comprise complementary overhangs of 4-30 bases; and (d) ligating the double-stranded DNA molecules of (c) by annealing the complementary overhangs to one another and ligating the ends of the products together using a ligase, thereby producing product molecules comprising molecules of the formula A-X-E-Y-F, A-X-B-Y-F, A-X-E-Y-C, D-X-B-Y-C, D-X-E-Y-C, and D-X-B-Y-F. In these embodiments, the sequences of A and D may be at least 80% identical, and the sequences of B and E may be at least 80% identical. In some embodiments, the product molecule of (d) may be circular.

Some embodiments of the method may comprise: (a) obtaining a first double-stranded DNA molecule of formula A and a second double-stranded DNA molecule of formula B; (b) nicking: (i) the first molecule of double-stranded DNA at a site that is 4-30 bases from the 3' end of one of the strands of the first molecule, using Cas9 nickase and a first guide RNA; (ii) the second molecule of double-stranded DNA at a site that is 4-30 bases from the 5' end of one of the strands of the second molecule, using Cas9 nickase and a second guide RNA; (c) denaturing the nicked products of (b) in moderately denaturing conditions, thereby producing double-stranded products that comprise overhangs in range of 10-30 bases in length; and (d) ligating the double-stranded products of (c) by annealing the overhangs to a splint oligonucleotide and ligating the ends of the products using a ligase, thereby joining the double-stranded products to the splint oligonucleotide and producing a product molecule of the formula A-B.

In these embodiments, the method may comprise: (a) obtaining a first double-stranded DNA molecule of formula A, a second double-stranded DNA molecule of formula B and a third double-stranded DNA molecule of formula C; (b) nicking: (i) the first double-stranded DNA molecule at a site that is 4-30 bases from an end of one of the strands of the first fragment, using Cas9 nickase and a first guide RNA; (ii) each end of the second double-stranded DNA molecule, at sites that are 4-30 bases away from a 3' or 5' terminus, using the Cas9 nickase and a second and third guide RNAs; (iii) the third double-stranded DNA molecule at a site that is 4-30 bases from an end of one of the strands of the third fragment, using the Cas9 nickase and a fourth guide RNA; (c) denaturing the nicked products of (b) in moderately denaturing conditions, thereby producing double-stranded products that comprise overhangs in range of 4-30 bases in length; and (d) ligating the double-stranded products of (c) by annealing the overhangs to a first splint oligonucleotide and a second splint oligonucleotide and ligating the ends of the products using a ligase, thereby joining the double-stranded products to the splint oligonucleotides and producing a product molecule of the formula A-B-C.

In any embodiment, the overhanging sequences made by CAS9 cleavage may be in the range of 4 to 30 bases in length, e.g., 18-23 bases in length.

In any embodiment, the denaturing may be done by raising the temperature to a temperature in the range of 60° C. to 90° C.

In any embodiment, the ligase used for ligation may be a thermostable ligase.

In any embodiment, the method may comprise filling in any gap after annealing and before ligating using a polymerase and one or more nucleotides.

In any embodiment, steps (c) and (d) multiple times (e.g., 5 to 50 times) in succession, thereby producing more product molecules.

In any embodiment, the first and second molecules are each of at least 100 bp (e.g., 100 bp to 1 kb, or longer) in length.

In any embodiment, the Cas9 nicking enzyme has amino acid substitutions at D10 or H840, or a site corresponding thereto.

In any embodiment, the nicking step (b) is done using a Cas9 nickase and guide RNAs that are complementary to opposite strands of the target sequence.

In any embodiment, the product molecule may comprise a coding sequence.

In any embodiment, steps (b) to (d) may be done in a single vessel and no additional reagents are added therebetween.

Example 1

In this example an assembly method that uses RNA-programmable nickases to generate nicks at defined positions near the ends of two double stranded DNA molecules is described. After gentle denaturation, these nicks are converted to ~18-23 nucleotide long single stranded ends that can then anneal together to facilitate assembly and ligation. The advantages of this method are 1) A nick can be made at a precise site to yield a single stranded end long enough to provide exquisite specificity for assembly. 2) The single stranded ends of DNA can be perfectly matched so that no DNA polymerase activity is required during assembly and therefore synthesis errors are avoided. 3) The length of the single stranded end is precisely defined so the total length of the DNA fragments to be assembled can closely approach the length of the single stranded end (i.e., total length ~50 nucleotides). 4) The conditions required to melt the short nicked ends can be controlled so that the entire DNA fragment remains intact, thus minimizing errors due to inadvertent hybridization.

For two DNA fragments to be ligated together by this method they may have a minimum amount of base pairs of homology (e.g., 16-21 bases) at their junction. This region of homology has to be flanked at the 5' end by a CCN trinucleotide and at the 3' end by a NGG trinucleotide (see FIG. 8). These sequences represent the PAM sequence motifs required for Cas9 target recognition. These sequence requirements are frequently fulfilled by natural DNA sequences, but can also be engineered into a junction. The region of homology is short enough that it can be added to a DNA fragment by overhang PCR. To generate the nicks, two guide RNAs (gRNAs) are generated that are complementary to one strand at each DNA fragment end. These gRNAs are loaded into Cas9 protein variants that carry an inactivating mutation in, e. g, the RuvC-like nuclease domain. The entire digestion and ligation reaction can be done in a single mix that contains A) the DNA fragments to be assembled B) the programmed Cas9 variants and C) a thermostable DNA ligase. At the beginning of the reaction, the programmed Cas9 proteins anneal the gRNA to the appropriate target and generate precise nicks in the complementary strands (FIG. 8). After digestion, the reaction temperature is raised appropriately to melt the short nicked fragment off of the DNA fragments (FIG. 9). Next, the temperature is reduced to allow the DNA fragment ends to anneal together (FIG. 10) and ligase then seals the nicks. Additional cycles of melting, annealing and ligation can be performed to drive the reaction to completion without addition of any further reagents.

FIG. 8 shows exemplary double stranded DNA sequences of two fragments to be joined. Target sequences that are complementary to gRNAs are underlined. PAM sequences are shown in bold. Nick sites are indicated by the I symbols. Underscores opposite of the I symbols are used in this illustration to keep the two strands in register. FIG. 9 shows nicked DNA fragments after melting. FIG. 10 shows nicked DNA fragments after annealing.

Example 2

In this example an assembly method that uses RNA-programmable nickases to generate nicks at defined positions near the ends of two double stranded DNA molecules is described. After gentle denaturation, these nicks are converted to ~18-23 nucleotide long single stranded ends that have no complementarity and are in the opposite orientation (i.e. one is a 5' overhang and the other a 3' overhang). To ligate these incompatible ends together, an additional single stranded DNA oligonucleotide (a "splint") is added that contains exact complementarity to the single stranded ends that are to be ligated together. These three DNA elements can anneal together to facilitate a desired assembly orientation and ligation. Use of an ssDNA bridge has been demonstrated for the ligation of 5' and 3' ssDNA overhangs generated by restriction enzymes (Zhao and Hortsch, BioTechniques 23:418-420 (1997)). The advantages of this method are: 1) No complementarity is required between the ends of the two DNA fragments to be ligated together. 2) A nick can be made at a precise site to yield a single stranded end long enough to provide exquisite specificity for assembly. 3) The three DNA elements can be perfectly matched so that no DNA polymerase activity is required during assembly and therefore synthesis errors are avoided. 4) The length of the single stranded end is precisely defined so the total length of the DNA fragments to be assembled can closely approach the length of the single stranded ends (i.e. total length ~50 nucleotides). 5) The PAM trinucleotide recognition sequence (CCN) of Cas9 occurs at high frequency in natural DNA sequences and presents only a weak constraint on assembly design. 6) The conditions required to melt the short nicked ends can be controlled so that the entire DNA fragment remains intact, thus minimizing errors due to inadvertent hybridization.

For two DNA fragments to be ligated together by this method they do not require any homology at their junction. Each end requires a CCN trinucleotide within 18-24 bp of the ends to be ligated (see FIG. 11). These sequences represent the PAM sequence motifs required for Cas9 target recognition. These sequence requirements are frequently fulfilled by natural DNA sequences, but can also be engineered into a junction. To generate the nicks, two guide RNAs (gRNAs) are generated that are complementary to one strand at each DNA fragment end. These gRNAs are loaded into Cas9 protein variants that carry an inactivating mutation in the RuvC-like nuclease domain (Jinek et al, Science 337; 816 (2012)). The entire digestion and ligation reaction can be done in a single mix that contains A) the DNA fragments to be assembled, B) the programmed Cas9 variants and C) a thermostable DNA ligase. At the beginning of the reaction, the programmed Cas9 proteins anneal the gRNA to the appropriate target and generate precise nicks in the complementary strands (FIG. 11). After digestion, the reaction temperature is raised appropriately to melt the short nicked fragment off of the DNA fragments (FIG. 12). Next, the temperature is reduced to allow the DNA fragment ends to anneal with the single-stranded DNA bridge (FIG. 13) and ligase then seals the nicks. In the example below, the target DNA sequence in fragment one is adjacent to the fragment end. If this placement interferes with Cas9 function, the target sequence can be selected farther from the fragment end, resulting in a longer ssDNA overhang.

FIG. 11 shows double stranded DNA sequences of two fragments to be joined. Target sequences that are complementary to gRNAs are underlined. PAM sequences are in bold. Nick sites are indicated by the / symbols. Underscores opposite of the / symbols are used in this illustration to keep the two strands in register. FIG. 12: Nicked DNA fragments after melting. FIG. 13: Nicked DNA fragments and ssDNA bridge (italics) after annealing.

What is claimed is:

1. A method of combining nucleic acid fragments, comprising:
   (a) providing two double-stranded DNA molecules having a common sequence, wherein the common sequence is at the end of each molecule;
   (b) nicking one strand in the common sequence of both molecules at a respective nicked site with one or more Cas9 nicking enzymes;
   (c) moderately denaturing both molecules to remove a single-stranded fragment from the nicked site to said end of each molecule, wherein the single-stranded fragment includes 4-30 bases of the common sequence, resulting in an overhanging sequence in each molecule, and the overhanging sequences in both molecules are complementary to each other; and
   (d) allowing the overhanging sequences of both molecules to anneal to each other, and ligating the molecules.

2. The method of claim 1, wherein the overhanging sequences of (c) are in the range of 18-23 bases in length.

3. The method of claim 1, wherein the denaturing is by raising the temperature to a temperature in the range of 60° C. to 90° C.

4. The method of claim 1, wherein the molecules are ligated in step (d) by a thermostable ligase.

5. The method of claim 4, wherein the method comprises repeating steps (c) and (d) multiple times.

6. The method of claim 1, wherein the first and second molecules are each of at least 100 bp in length.

7. The method of claim 1, wherein the one or more Cas9 nicking enzymes has amino acid substitutions at D10 or H840, or a site corresponding thereto.

8. The method of claim 1, wherein the nicking step (b) is done by the one or more Cas9 nickases and guide RNAs that are complementary to opposite strands of the common sequence.

9. The method of claim 1, wherein the product of step (d) comprises a coding sequence.

10. The method of claim 1, wherein steps (b) to (d) are done in a single vessel and no additional reagents are added between steps (b) to (d).

11. A method for recombining DNA molecules, comprising:
    (a) obtaining a first double-stranded DNA molecule of formula A and a second double-stranded DNA molecule of formula B;
    (b) nicking:
       (i) the first molecule of double-stranded DNA at a site that is 4-30 bases from the 3' end of one of the strands of the first molecule, using Cas9 nickase and a first guide RNA;
       (ii) the second molecule of double-stranded DNA at a site that is 4-30 bases from the 5' end of one of the strands of the second molecule, using Cas9 nickase and a second guide RNA;
    (c) denaturing the nicked products of (b) in moderately denaturing conditions, thereby producing double-stranded products that comprise overhangs in range of 10-30 bases in length; and
    (d) ligating the double-stranded products of (c) by annealing the overhangs to a splint oligonucleotide and ligating the ends of the products with a ligase, thereby joining the double-stranded products to the splint oligonucleotide and producing a product molecule of the formula A-B.

12. The method of claim 11, wherein the overhanging sequences of (c) are in the range of 18-23 bases in length.

13. The method of claim 11, wherein the denaturing is by raising the temperature to a temperature in the range of 60° C. to 90° C.

14. The method of claim 11, wherein the ligase used in step (d) is a thermostable ligase.

15. The method of claim 14, wherein the method comprises repeating steps (c) and (d) multiple times.

16. The method of claim 11, wherein the first and second molecules are each of at least 100 bp in length.

17. The method of claim 11, wherein the Cas9 nicking enzyme has amino acid substitutions at D10 or H840, or a site corresponding thereto.

18. The method of claim 11, wherein the nicking step (b) is done by the Cas9 nickase and guide RNAs that are complementary to opposite strands of the common sequence.

19. The method of claim 11, wherein steps (b) to (d) are done in a single vessel and no additional reagents are added between steps (b) to (d).

* * * * *